United States Patent [19]

Giordano

[11] Patent Number: 6,107,029

[45] Date of Patent: *Aug. 22, 2000

[54] UNIVERSAL METHOD FOR DETECTING INTERACTIONS BETWEEN RNA MOLECULES AND RNA BINDING PROTEINS

[75] Inventor: Tony Giordano, Phoenixville, Pa.

[73] Assignee: Message Pharmaceuticals, Inc., Malvern, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/690,010

[22] Filed: Jul. 31, 1996

[51] Int. Cl.$^7$ ..................................................... C12N 15/00

[52] U.S. Cl. .................................. 435/6; 435/6; 435/810; 435/5; 436/501

[58] Field of Search ................................... 435/6, 810, 5; 436/501; 935/77, 78

[56] References Cited

U.S. PATENT DOCUMENTS

| | | |
|---|---|---|
| 3,625,214 | 12/1971 | Higuchi . |
| 4,789,734 | 12/1988 | Piershbacher . |
| 4,906,474 | 3/1990 | Langer et al. . |
| 4,925,673 | 5/1990 | Steiner et al. . |
| 5,525,495 | 6/1996 | Keene et al. . |

FOREIGN PATENT DOCUMENTS

WO 94/09792  5/1994  WIPO .

OTHER PUBLICATIONS

Ausubel et al., "Synthesizing Proteins in vitro by Translation of Cloned Genes," *Current Protocols in Molecular Biology*, pp. 10.17.1–10.17.5 (John Wiley & Sons, Inc., 1996).
Burd, et al., "Conserved Structures and Diversity of Functions of RNA–Binding Proteins," *Science* 265:615–621 (1994).
Current Protocol in Molecular Biology, Section VII, pp. 10.17.1–10.17.5 (John Wiley & Sons, Inc. 1989).
Eberwine, J.H., et al., "mRNA Structure, In Situ, as Assessed by Microscopic Techniques" *Microscopy Research and Technique* 25:19–28 (1993).
Gregoriadis, Chapter 14. "Liposomes", *Drug Carriers in Biology and Medicine* pp. 287–341 (Academic Press, 1979).
Johnstone, et al., "Production of Antibodies," *Immunichemistry in Practice*, pp. 30–34; pp. 234–240 (Blackwell Scientific Publications, 1987).
Malter, *Science* 240:668–670 (1989).
Rodriguez, et al., "Biotin–Labeled Riboprobes to Study RNA–Binding Proteins," *Biomethods* 7:215–225 (1996).
Rouault et al., "The Iron–Responsive Element Binding Protein: A Method for the Affinity Purification of a Regulartoy RNA–Binding Protein," *Proc. Natl. Acad. Sci. USA* 86:5768–5772 (1989).
Zaidi, et al., "Nucleolin and heterogeneous nuclear ribonucleoprotein C proteins specifically interact with the 3'–untranslated region of amyloid protein precursor mRNA," *J. Biol. Chem.* 270(29):17292–17298 (1991).
Samuels et al. (1994) Mol. Cell. Biol. 14:4975–4900.
Pause et al. (1993) Mol. Cell. Biol. 13:6789–98.
Galarza et al. (1992) Virus Res. 24:91–106.
Xing et al. (1995) J. Mol. Biol. 249:319–331.
Bienroth et al. (1993) EMBO J. 12:585–94.
Hanker (1990) Radioisotopy 31:213–20 (abstract in English).
Carey et al. (1983) Biochemistry 22:2601–10.
Ghosh et al. (1994) Nucleic Acids Res. 22:1663–69.
Spierer et al. (1978) Biochemistry 17:5394–98.
Gale et al. (1995) Biochemistry 34:8896–8903.
Uhlenbeck et al. (1983) J. Biomol. Structure Dynam. 1:539–552.
Romaniuk et al. (1987) Biochemistry 26: 1563–68.
Witherell et al. (1989) Biochemistry 28:71–76.
Cole et al. (1995) Biochemistry 32:11769–75.
Chen et al. (1995) Proc. Natl. Acad. Sci. USA 92:5077–81.
Wu et al. (1993) Biochemistry 32:4761–68.
Ashley, C.T., et al. "FMR1 Protein: Conserved RNP Family Domains and Selective RNA Binding" *Science* 262:563–566 (Oct. 1993).
Smith J.A. Analysis of Proteins: *Current Protocols in Molecular Biology* 2:Supp.21.
Baer, M.L., et al. "Specific RNA Binding by Amino–terminal Peptides of Alfalfa Mosaic Virus Coat Protein" *EMBO Journal* 13(3):727–735 (1994).
Bass, B.L. "Double–stranded RNA Binding Proteins and Their Substrates" *Nucleic Acids Symposium Series No. 13* 13–15.
Bohjanen, P.R., et al. "An Inducible Cytoplasmic Factor (AU–B) Binds Selectively to AUUUA Multimers in the 3' Untranslated Region of Lymphokins mRNA" *Mol. Cell. Biol.* 11(6):3288–3295 (Jun. 1991).

(List continued on next page.)

*Primary Examiner*—Stephanie W. Zitomer
*Attorney, Agent, or Firm*—Clark & Elbing LLP

[57] ABSTRACT

It has been discovered that a single set of conditions can be used to detect nearly every interaction of RNA binding proteins and RNA molecules. Prior to this discovery it was thought that each specific interaction required separate optimized conditions in order to be detected. Assays employing the disclosed universal conditions are useful for identifying RNA binding proteins that interact with specific RNA molecules of interest, detecting RNA molecules that interact with specific RNA binding proteins of interest, identifying RNA binding proteins active in certain cell types and under certain physiological conditions, identifying specific regions of an RNA molecule that interact with RNA binding proteins. Such assays are useful as a research tool for identifying targets for drug discovery, identifying altered or defective RNA/RBP interactions associated with disease conditions, and in screening assays to identify compounds that modulate RNA/RBP interactions of interest.

34 Claims, 3 Drawing Sheets

OTHER PUBLICATIONS

Brewer, G. "An A + U –Rich Element RNA–Binding Factor Regulates c–myc mRNA Stability in vitro" *Mol. Cell. Biol.* 11(5):2460–2466 (May 1991).

Carey, J. and Uhlenbeck, O. "Kinetic and Thermodynamic Characterization of the R17 Coat Protein–Ribonucleic Acid Interaction"*Biochemistry* 22:2610–2615 (1983).

Gillis, P. and Malter, J. "The Adenosine–Uridine Binding Factor Recognizes the AU–rich Elements of Cytokine, Lymphokine, and Oncogene mRNAs*" *J. Biol. Chem.* 266(5):3172–3177 (1991).

Görlach, M., et al. "The Determinants of RNA–binding Specificity of the Heterogeneous Nuclear Ribonucleoprotein C Proteins*" *J. Biol. Chem.* 269(37):23074–23078 (Sep. 1994).

Hamilton, B.J. "Association of Heterogeneous Nuclear Ribonucleoprotein A1 and C Proteins with Reiterated AUUUA Sequences*" *J. Biol. Chem.* 268(12):8881–8887 (Apr. 1993).

Henics, T., et al. "Combined Application of in vitro UV–Crosslinking and in vitro Label, Transfer in the Examination of AU–Rich Sequence Binding Protin—RNA Interactions" *Cell Biology International* 19(9):791–801 (1995).

Herbert, A., et al. "Chicken Double stranded RNA Adenosine Deaminase has Apparent Specificity of Z–DNA" *Proc. Natl. Acad. Sci. USA* 92:7550–7554 (Aug. 1995).

Hoy et al., "Bromodeoxyuridine/DNA Analysis of Replication in CHO Cells After Exposure to UV Light" *Mutation Research,* 290:217–230 (1993).

Kerkhof, L. "A Comparison of Substrates for Quantifying the Signal from a Nonradiolabeled DNA Probe" *Analyhtical Biochemistry* 205:359–364 (1992).

Kiledjian, M., et al. "Identification of Two KH Domain Proteins in the α–globin mRNP Stability Complex" *The EMBO Journal* 14(17):4357–4364 (1995).

Langer, et al., "Enzymatic Synthesis of Biotin–Labeled Polynucleotides: Novel Nucleic Acid Affinity Probes," *Proc. Natl. Acad. Sci. USA,* 73:6633 (1981).

Malter, J. "Identification of an AUUUA–Specific Messenger RNA Binding Protein" *Science* 246:664–666 (Nov. 1989).

Neupert, B., et al. "A High Yield Affinity Purification Method for Specific RNA–binding Proteins: Isolation of the Iron Regulatory Factor from Human Placenta" *Nucleic Acids Research* 18(1):51–55 (1990).

Oberste, M.S. and Flanegan, J.B. "Measurement of Poliovirus RNA Polymerase Binding to Plliovirion and Nonviral RNAs Using a Filter–binding Assay" *Nucleic Acids Research* 16 (21):10339–10352 (1988).

Rondon, I.J., et al. "Hypoxia Up–regulates the Activity of a Novel Erythropoietin mRNA Binding Protein*" *J. Bio. Chem.* 266(25):16594–16598 (Sep. 1991).

Sambrook, J., et al. *Molecular Cloning* Cold Spring Harbor Laboratory Press 2nd Ed. (1989).

Scripture, J.B. and Huber, P.W. "Analysis of the Binding of *Xenopus* Ribosomal Protein L5 to Oocyte 5 S rRNA"*J. Bio. Chem.* 270(45):27358–27365 (Nov. 1995).

Shen, Q., et al. "RNA–binding Proteins That Specifically Recognize the Selenocysteine Insertion Sequence of Human Cellular Glutathione Peroxidase mRNA*" *J. Bio. Chem.* 270(51):30448–30452 (Dec. 1995).

Wansink, D.G., et al. "Fluorescent Labeling of Nascent RNA Reveals Transcription by RNA Polymerase II in Domains Scattered Throughout the Nucleus" *J. Cell Bio.* 122(2):283–293 (Jul. 1993).

Yu, et al., "Cyuanine Dye dUTP Analogs for Enzymatic Labeling of DNA Probes," *Nucleic Acids Res.,* 22:3226–3232 (1994).

Zaidi, S.H.E. and Malter, J.S. "Amyloid Precursor Protein mRNA Stability is Controlled by a 29–Base Element in the 3'–Untranslated Region*" *J. Bio. Chem.* 269(39):24007–24013 (Sep. 1994).

Zaidi, S.H.E., et al. "Multiple Proteins Interact at a Unique cis–Element in the 3'–Untranslated Region of Amyloid Precursor Protein mRNA*" *J. Biol. Chem.* 269(39)24000–24006 (Sep. 1994).

Zhang, W., et al "Purification, Characterization, and cDNA Cloning of an AU–Rich Element RNA–Binding Protein, AUF1" *Mol. Cell. Bio.* 13(12):7652–7665 (Dec. 1993).

UNIVERSAL METHOD FOR DETECTING INTERACTIONS BETWEEN RNA MOLECULES AND RNA BINDING PROTEINS

BACKGROUND OF THE INVENTION

The invention is in the area of assays for detecting interactions between RNA and RNA binding proteins.

The regulation of protein function can occur at a number of levels: transcriptional, post-transcriptional, or post-translational. The modulation of protein function is often critical for the treatment of disease. Recent work at modulating protein levels by altering transcriptional activity has resulted in preclinical research programs being established and licensing agreements being entered into. For example, Ligand Pharmaceuticals, Inc. (San Diego, Calif.) has entered into multiple drug discovery programs with large pharmaceutical companies based on their Signal Transducers and Activators of Transcription technology for use as anti-inflammatory, anti-cancer and hormone replacement therapies. In addition, Oncogene Science, Inc. (Uniondale, N.Y.) is using its proprietary gene transcriptional technologies to develop biopharmaceutical products for the treatment of cancer. Other companies, such as Signal Pharmaceuticals, Inc. (San Diego, Calif.) and Tularik, Inc. (San Francisco, Calif.) are developing small molecules that regulate transcription factors. While this approach holds promise, no compounds have yet to make it to clinical trials. The lack of specificity of transcription factors and requirement for nuclear localization are two concerns with this technology. In the first case, a drug affecting the binding of a transcription factor may affect transcription of many genes other than the target gene. In the second case, it is difficult to design a drug that both has the proper interaction with a targeted transcription factor and is transported into the nucleus where it exerts its effect. Inhibition of protein expression by targeting the RNA is an alternate approach involving antisense technology. The antisense technology has also generated much interest with several products in clinical trials (ISIS2105, ISIS2922 and ISIS2302). However, the major drawbacks with this approach are the cost of oligonucleotides, the ability to deliver the oligonucleotides into cells, and their inability to increase protein levels.

A major area of post-transcriptional regulation in eukaryotic cells involves the specific interaction of proteins with RNA. These RNA binding proteins (RBP) appear to mediate the processing of pre-mRNAs, the transport of mRNA from the nucleus to the cytoplasm, mRNA stabilization, the translational efficiency of mRNA, and the sequestration of some mRNAs. Recent studies have identified several RNA-binding motifs in a diversity of RBPs. The most common RNA binding protein motifs are the RNP motif, Arg-rich motif, RGG box, KH motif and double-stranded RNA-binding motif (for review see Burd and Dreyfuss, *Science* 265:615–621 (1994)). These motifs recognize both sequence and structure dependent RNA elements. In the case of the double-stranded RNA-binding motif, sequence recognition is unimportant. However, in addition to the double stranded structure, a positional effect for the double-stranded RNA may play a role in recognition (Bass, *Nucleic Acids Symposium* 33:13–15 (1995)) and some of these proteins may also require binding to Z-DNA prior to their activity on the double-stranded RNA (Herbert et al., *Proc. Natl. Acad. Sci. USA* 92:7550–7554 (1995)). In addition, other RNA binding proteins, such as AUBF (Malter, *Science* 246:664–666 (1989)) are likely to bind in a structure-independent manner.

Due to the clear importance of RNA/RBP interactions in the regulation of gene expression, these interactions would be an attractive target for drugs that affect them for modulation of protein levels in disease states. To fully exploit these interactions as therapeutic targets, however, requires a clear understanding of how these interactions affect expression, which RBPs are involved in the regulation of RNAs of interest, and the ability to study the modulating effects of potential drugs on the RNA/RBP interactions.

Many investigators have used mobility shift assays to detect RNA/protein interactions. However, the conditions established in one laboratory often fail to detect interactions of different molecules. In addition, the diversity of RNA structures and binding motifs in the protein have led numerous investigators to conclude that a single set of conditions would be impossible to define for detection of multiple different interactions. With more genes being identified as being post-transcriptionally regulated, a universal set of binding conditions would allow for the detection and characterization of the molecules involved in these interactions and ultimately would provide targets for which therapeutics could be developed. No such universal assay conditions have been previously described for the identification of RNA binding proteins, the RNA molecules and RNA-binding sites with which they interact, and the study of these interactions.

Due to the variety of RBPs and motifs it has generally been required that individual assay conditions be painstakingly worked out for each RNA/RBP combination, resulting in slow progress in studying known RBPs and their interactions and in slowed or prevented identification of additional RBPs and their RNA motifs. Clearly, some RNA/RBP interactions have gone undetected simply because the right assay conditions have never been tried. Thus, there is a need for more universal assay conditions which can be expected to detect the majority of specific RNA/RBP interactions.

Therefore, it is an object of the invention to provide an assay for detecting interactions between any RNA binding protein and its cognate RNA binding site.

It is a further object of the invention to provide an assay for identifying RNA molecules that interact with an RNA binding protein.

It is a further object of the invention to provide an assay for identifying RNA binding proteins that interact with an RNA molecule.

It is a further object of the invention to provide an assay for identifying genes coding for RNA molecules that interact with a given RNA binding protein.

It is a further object of the invention to provide an assay for determining if an RNA molecule encoded by a gene interacts with one or more RNA binding proteins.

It is a further object of the invention to provide an assay for identifying regions in an RNA molecule encoded by a gene that interact with RNA binding proteins.

It is a further object of the invention to provide a method of screening for compounds that modulate interaction of RNA binding proteins and RNA molecules.

It is a further object of the invention to provide an assay for detecting if RNA molecules that interact with an RNA binding protein are present in a sample.

It is a further object of the invention to provide an assay for detecting if RNA binding proteins that interact with an RNA molecule are present in a sample.

It is a further object of the invention to provide a kit for an assay for detecting interactions between RNA binding proteins and RNA molecules.

SUMMARY OF THE INVENTION

It has been discovered that a single set of conditions can be used to detect nearly every interaction of RNA binding proteins and RNA molecules. Prior to this discovery it was thought that each specific interaction required separate optimized conditions in order to be detected. Assays employing the disclosed universal conditions are useful for identifying RNA binding proteins that interact with specific RNA molecules of interest, detecting RNA molecules that interact with specific RNA binding proteins of interest, identifying RNA binding proteins active in certain cell types and under certain physiological conditions, and identifying specific regions of an RNA molecule that interact with RNA binding proteins. Such assays are useful as a research tool for identifying targets for drug discovery, identifying altered or defective RNA/RBP interactions associated with disease conditions, and in screening assays to identify compounds that modulate RNA/RBP interactions of interest.

DETAILED DESCRIPTION OF THE INVENTION

Disclosed are universal conditions and procedures that can be applied to any RNA molecule and any RNA binding protein to detect interactions between them. The basic detection procedure can be adapted to detect interactions between RNA binding proteins and RNA molecules in bulk, interactions between RNA binding proteins and a specific RNA molecule, and interactions between RNA molecules and a specific RNA binding protein. The detection procedure can thus be used to, for example, detect all of the RNA binding proteins present in a sample, such as a cell or tissue extract, with a specific RNA molecule, such as the transcript from a gene of interest. Similarly, the detection procedure can be used to detect all of the RNA molecules present in a sample, such as a cell or tissue extract, with a specific RNA binding protein.

The detection procedure, and a kit therefor, is useful as a research tool, both for identifying interactions between RNA molecules and RNA binding proteins, and for identifying compounds that modulate such interactions. Compounds identified in such a screening assay could be useful for regulating the expression of RNA molecules of interest. The importance of interactions between RNA molecules and RNA binding proteins was described above. All of the uses can be accomplished by applying the basic detection procedure and specific adaptions of the basic detection procedure as described herein.

It has been discovered that a single set of conditions can be used to detect nearly every interaction of RNA binding proteins and RNA molecules. These conditions allow detectable complexes between RNA binding proteins and RNA molecules and are thought to mimic physiological conditions in cells where such interactions normally occur. Prior to this discovery it was thought that each specific interaction required separate optimized conditions in order to be detected.

As used herein, interactions between RNA binding proteins and RNA molecules which are referred to as "possible" are intended to mean those interactions which are specific and which occur under at least one set of conditions (e.g. in vivo or optimized binding assay conditions). In the context of the disclosed universal method of detecting interactions between RNA binding proteins and RNA molecules, the method will detect a majority of the interactions between RNA binding proteins and RNA molecules which are possible. The meaning of the term "specific interaction" is generally understood to mean interactions that are based on specific characteristics of the interacting molecules and not on general characteristics. For example certain RNA binding proteins recognize and bind specifically to sites in RNA molecules having the nucleotide sequence AUUUA. This is a specific interaction. Conversely, some proteins bind RNA molecules in general (i.e. non-specifically) based on the general chemical characteristics of all RNA molecules. In general, an interaction can be identified as a non-specific interaction by determining that the interaction can be prevented in the presence of a non-specific competitor.

I. Components

A. Binding Solution

Interactions between RNA binding proteins and RNA molecules are facilitated in a binding solution. The binding solution contains one or more RNA molecules and buffer components. The buffer components include a buffer, a monovalent cation, a divalent cation, a reducing agent, and a density agent. It is preferred that the buffer is Bis-Tris Propane at a pH of about 8.5 and at a concentration of about 7.5 mM, the monovalent cation is $K^+$ at a concentration of about 50 mM, the divalent cation is $Mg^{++}$ at a concentration of about 1 mM, the reducing agent is dithiothreitol at a concentration of about 0.2 mM, and the density agent is glycerol at a concentration of about 10 percent (v/v).

These conditions have been optimized to be universally applicable. It is most preferred that the optimum conditions be used. However, one, or less preferably two, of the buffer components can be varied in the manner disclosed below. For varying certain buffer components, it is preferred that (1) the buffer is HEPES, Tris, or Bis-Tris Propane, each at a pH between about 8 and 10 and at a concentration of between about 5 and about 100 mM, (2) the monovalent cation is $K^+$, $Na^+$, or $NH_4^+$, each at a concentration of between 0 and about 100 mM, (3) the divalent cation is $Mg^{++}$, $Ca^{++}$, or $Fe^{++}$, each at a concentration of between 0 and about 5 mM, (4) the reducing agent is dithiothreitol or β-mercaptoethanol, at a concentration of between 0 and about 1 mM, and the density agent is glycerol or polyethylene glycol at a concentration of between 0 and about 20 percent (v/v).

For most RNA molecules, the reducing agent does not appear to be critical, although there is a trend to slightly better binding in the presence of a reducing agent, preferably DTT. However, in some cases the reducing agent makes a significant difference in the detection of interactions. Accordingly, the use of a reducing agent is preferred. A density agent does not appear to be required for detecting the interaction between RNA molecules and RNA binding proteins. However, when interactions are analyzed by gel mobility shift, the presence of a density agent does enhance the quality of the bands. Accordingly, the use of a density agent is preferred.

The binding solution can include other components that aid in the formation of specific interactions. For example, a competitor of non-specific RNA/protein interactions can be added to reduce the background of non-specific interactions. Poly r(G), tRNA, and heparin, are preferred competitors of non-specific RNA/protein interactions.

It is intended that a concentration range stated as between 0 and about a specific concentration does not encompass a concentration of zero but does encompass the specific concentration and concentrations up to about about 10% greater than the second specific concentration. It is also intended that a concentration range stated as between about a first specific concentration and about a second specific concentration encompasses the first specific concentration, concentrations up to about 10% lower than the first specific concentration, concentrations between the first and second specific concentrations, the second specific concentration, and concentrations up to about 10% greater than the second specific concentration. It is intended that a concentration range stated as from a first specific concentration to a second specific concentration encompasses the first specific concentration, concentrations between the first and second specific concentrations, and the second specific concentration. It is also intended that a concentration range stated as from 0 to a specific concentration encompasses a concentration of zero, concentrations between zero and the specific concentration, and the specific concentration.

Unless otherwise noted, all concentrations of buffer components are intended to be the final concentration of these components in a completely formed binding solution. The binding buffer can be formed by any combination of components that results in the intended final concentration. For example, a binding solution can be formed by mixing together, with other components of the binding solution, a single stock solution of buffer components, separate stock solutions of buffer components, or separate stock solutions of combinations of some of the buffer components. It is also intended that the final concentration of buffer components can be achieved by mixing different solutions each containing a part of the total amount of a given component. For example, part of the divalent cation can be added as part of a stock solution and part can be added with the RNA.

It is preferred that the concentration of extraneous compounds be kept to a minimum in binding solutions. It is understood, however, that samples of RNA binding proteins and RNA molecules may contain additional compounds. The concentration in the binding solution of such compounds can be reduced by, for example, diluting the sample to the greatest extent possible when forming the binding solution.

B. RNA Binding Proteins

RNA binding proteins for use in the disclosed method can be part of a crude cellular or nuclear extract, partially purified, or extensively purified. RNA binding proteins can be used either in isolation or in combination with one or more other RNA binding proteins. When the goal is to identify RNA binding proteins in a sample, it is preferred that the sample be an unpurified or partially purified extract so that the largest variety of RNA binding proteins will be present. When the goal is to identify RNA molecules, or portions of an RNA molecule, that interact with a specific RNA binding protein, it is preferred that the RNA binding protein be substantially purified.

RNA binding proteins can be prepared using known methods for preparing cellular extracts and for purifying proteins. Methods for preparing extracts containing RNA binding proteins and for purifying known RNA binding proteins are described in, for example, Ashley et al., *Science* 262:563–566 (1993), Rouault et al., *Proc. Natl. Acad. Sci. USA* 86:5768–5772 (1989), Neupert et al., *Nucleic Acids Research* 18:51–55 (1990), Zhang et al., *Molecular and Cellular Biology* 13:7652–7665 (1993), and references cited in Burd and Dreyfuss, *Science* 265:615–621 (1994). Individual RNA binding proteins can also be produced recombinantly using known techniques. DNA encoding RNA binding proteins can be obtained from known clones, by synthesizing a DNA molecule encoding an RNA binding protein with a known amino acid sequence, or by cloning the gene encoding the RNA binding protein. Techniques for recombinant expression of proteins and methods for cloning genes encoding known proteins are described by, for example, Sambrook et al., *Molecular Cloning* (Cold Spring Harbor Laboratory, 1989).

Detection of interactions between RNA binding proteins and RNA molecules can be facilitated by attaching a detectable label to the RNA binding protein. Generally, labels known to be useful for proteins can be used to label RNA binding proteins. Preferred labels for RNA binding proteins are $^{125}I$, $^3H$, and $^{35}S$. When the RNA binding protein is made recombinantly, it can be labeled by incorporation of labeled amino acids. Techniques for labeling and detecting labeled proteins are well known and are described in, for example, Sambrook et al., and Ausubel et al., *Current Protocols in Molecular Biology* (John Wiley & Sons, Inc., 1996). Detection of RNA binding proteins can also be accomplished with antibodies specific for the RNA binding protein. The production and use of antibodies for this purpose is well known and is described in, for example, Johnstone and Thorpe, *Immunochemistry in Practice* (Blackwell Scientific Publications, 1987).

C. RNA Molecules

RNA molecules for use in the disclosed method can be part of a crude cellular or nuclear extract, partially purified, or extensively purified. RNA molecules can also be made by in vitro transcription or by direct synthesis. RNA molecules can be used either in isolation or in combination with one or more other RNA molecules. When the goal is to identify RNA molecules in a sample, it is preferred that the sample be an unpurified or partially purified extract so that the largest variety of RNA molecules will be present. When the goal is to identify RNA binding proteins that interact with a specific RNA molecules, it is preferred that the RNA molecules be substantially purified. For this purpose, it is most preferred that the RNA molecule be produced in vitro.

RNA molecules can be prepared using known methods for preparing cellular extracts and for purifying RNA. Methods for preparing extracts containing RNA molecules are described in, for example, Sambrook et al., and Ausubel et al. Individual RNA molecules can also be produced recombinantly using known techniques, by in vitro transcription, and by direct synthesis. For recombinant and in vitro transcription, DNA encoding RNA molecules can be obtained from known clones, by synthesizing a DNA molecule encoding an RNA molecule, or by cloning the gene encoding the RNA molecules. Techniques for in vitro transcription of RNA molecules and methods for cloning genes encoding known RNA molecules are described by, for example, Sambrook et al.

Detection of interactions between RNA binding proteins and RNA molecules can be facilitated by attaching a detectable label to the RNA molecule. Generally, labels known to be useful for nucleic acids can be used to label RNA molecules. Examples of suitable labels include radioactive isotopes such as $^{33}$P, $^{32}$P, and $^{35}$S, fluorescent labels such as fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, and biotin.

Labeled nucleotides are the preferred form of label since they can be directly incorporated into the RNA molecules during synthesis. Examples of detection labels that can be incorporated into amplified RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.* 22:3226–3232 (1994)). A preferred nucleotide analog label for RNA molecules is Biotin-14-cytidine-5'-triphosphate. Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into RNA molecules, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.).

II. Method

The basic method for detecting interactions between RNA molecules and RNA binding proteins involves forming a binding solution containing the RNA molecules and IX binding buffer, heating the binding solution to denature the RNA molecules, cooling the binding solution to the reaction temperature, adding the RNA binding proteins to the binding solution, and detecting the interactions between the RNA molecules and the RNA binding proteins.

A. Forming the Binding Solution

The binding solution contains one or more RNA molecules, buffer components, and non-specific competitors. The buffer components include a buffer, a monovalent cation, a divalent cation, a reducing agent, and a density agent. The binding solution is formed by combining and/or mixing together the constituents of the binding solution in any manner that results in a binding solution having the required composition. The binding buffer can be formed by any combination of components that results in the intended final concentration. For example, a binding solution can be formed by mixing together, with other components of the binding solution, a single stock solution of buffer components, separate stock solutions of buffer components, or separate stock solutions of combinations of some of the buffer components. It is also intended that the final concentration of buffer components can be achieved by mixing different solutions each containing a part of the total amount of a given component. For example, part of the divalent cation can be added as part of a stock solution and part can be added with the RNA. Thus, the manner in which the final composition of the binding solution is arrived at is not critical. It is intended that any combination of solutions and components that achieves this result is encompassed by this step.

B. Heating and Cooling the Binding Solution

The formed binding solution is heated and cooled in order to denature any higher order structure in the RNA molecules. Such structures can make the RNA molecules less accessible to the RNA binding proteins. When using RNA molecules purified from natural sources, it is also possible that other molecules can remain bound to the RNA. The heating step can serve to release such molecules. The heating and cooling step involves subjecting the binding solution to a heat source until it reaches a sufficient temperature, and then allowing the solution to cool to the reaction temperature. The temperature to which the binding solution is heated can be any temperature that will substantially denature the RNA molecules present in the binding solution. It is understood that different temperatures will be sufficient for different RNA molecules. For example, shorter RNA molecules and RNA molecules with a low GC content will, in general, be substantially denatured at lower temperatures. However, it is preferred that a single temperature be used for the heating step. In this case, it is preferred that a temperature sufficient to substantially denature RNA molecules in general be used. A preferred temperature is 65° C. After allowing the solution to cool to the reaction temperature, the RNA binding protein is added to the binding solution prior to incubation at the appropriate temperature for RNA-protein binding, preferably 37° C.

C. Detecting Interactions

Interactions between RNA binding proteins and RNA molecules can be detected using any suitable procedure. It is preferred that detection involve separation of interacting RNA molecules and RNA binding proteins. This can be accomplished, for example, by separating components in the binding solution on the basis of size or physical properties. Two preferred methods of separation and detection of interacting RNA molecules and RNA binding proteins are filter binding and gel mobility shift.

1. Filter binding involves trapping interacting molecules on a filter while non interacting molecules pass through the filter. This procedure is known to those of skill in the art. For example, prewet nitrocellulose filters are equilibrated in 1× binding buffer. The binding reaction is then applied to the filter by vacuum filtration to remove unbound RNA. The filter is washed in 1× binding buffer, scintillation cocktail is added and the amount of protein-bound RNA is determined by scintillation counting.

2. Gel mobility shift involves resolving interacting and non-interacting RNA molecules and RNA binding proteins on a gel by electrophoresis and visualizing the location and amount of components that migrate to different extents. Interacting RNA molecules and RNA binding proteins tend to migrate less in the gel than non-interacting molecules by virtue of their greater mass. Gel mobility shift assays can be performed as follows. After incubation of the binding reaction, 6× loading buffer (30% glycerol, 0.25% xylene cyanol, 0.25% bromophenol blue) is added to a final concentration of 1×. The reaction is then loaded into the wells of a polyacrylamide gel (generally 4 to 8%) prepared in TBE buffer (90 mM Tris-borate, 2 mM EDTA, pH 8). The protein-bound RNA is separated from the unbound RNA by applying a constant voltage (150 to 175 V) to the gel and allowing the gel to run until the bromophenol blue has reached the bottom of the gel. The gel is the dried in vacuo at 80° C. The unbound RNA and the protein-bound RNA is then visualized autoradiographically. In cases where it is desirable to know the molecular weight of the RNA-protein complex, the binding reaction is subjected to ultraviolet light to covalently crosslink the complex. 6× loading buffer (3.75 M Tris, 30% βME, 13.8% SDS, 30% glycerol, pH 6.8) is added to the crosslinked reaction at a final concentration of 1× and the mixture is loaded onto a SDS-polyacrylamide gel (generally 8 to 12%). The gel is run in a Tris-glycine buffer (25 mM Tris, 192 mM glycine, 0.1 % SDS) at 30 mA until the molecular weight markers are adequately separated. The gel is dried and the RNA-protein complex visualized autoradiographically.

3. Ribonuclease digestion. For some assays it may be desirable to eliminate those RNA molecules, or those regions of an RNA molecule, that are not involved in an interaction with RNA binding proteins. For example, when a large RNA molecule is used in the assay, binding of an RNA binding protein might result in an RNA/protein complex only slightly larger than the RNA molecule alone. When detecting such a complex by gel mobility shift, the resulting shift may not be easily detectable. When detecting such a complex by filter binding, the RNA molecule alone may be sufficiently large to be retained by the filter. Such potential problems can be mitigated by digesting RNA not involved in interactions. This is easily accomplished by subjecting the binding solution to ribonuclease digestion. Only the unbound or non-interacting RNA will be digested. The regions of RNA bound by RNA binding proteins will be protected from digestion by the protein.

D. Identifying RNA Molecules and RNA Binding Molecules That Interact With Specific RNA Binding Proteins and RNA Molecules Identification of RNA molecules that interact with a specific RNA binding protein can be accomplished by forming a binding solution comprising one or more RNA molecules, and buffer components comprising a buffer, a monovalent cation, a divalent cation, a reducing agent, and a density agent, adding the specific RNA binding protein, and detecting interactions between the one or more RNA molecules and the RNA binding protein. Those RNA molecules that interact can be identified by specific sequence analysis. An assay of this type can be used to identify all those RNA molecules in a given sample which are specific for an RNA binding protein of interest. The identification of such RNA molecules can lead to the identification of genes encoding RNA molecules regulated by the RNA binding molecules of interest.

In a similar way, RNA binding proteins that interact with a specific RNA molecule can be identified by forming a binding solution comprising the RNA molecule of interest, and the buffer components, adding one or more RNA binding proteins, and detecting interactions between the one or more RNA binding proteins and the RNA molecule.

E. Identifying Genes Encoding RNA Molecules That Interact With RNA Binding Proteins The genes encoding RNA molecules that interact with RNA binding proteins can be identified by synthesizing a labeled cDNA from the RNA molecule and using the cDNA to screen a library of genes thought to contain the gene encoding the RNA molecule. The gene encoding the RNA molecule can then be identified by sequence analysis. The identity of the gene can be confirmed by determining the intron-exon structure of the gene, cloning the exons into a vector and transcribing the RNA in vitro. The in vitro transcribed RNA can then be used to form a binding solution, and the interactions with the RNA binding proteins can be detected and compared with the interactions of the original RNA and RNA binding protein. The gene is confirmed as encoding the RNA molecule if the interactions between the test RNA and the RNA binding proteins are substantially the same as those of the original RNA and the RNA binding proteins. Procedures for all of these manipulations are well established and known to those of skill in the art and/or are described herein.

F. Identifying Genes Encoding RNA Binding Proteins

The genes encoding RNA binding proteins that interact with RNA molecules can be identified by isolating the binding protein and determining a portion of the amino acid sequence, This sequence can then be used to generate peptides which in turn can be used to produce antibodies to the RNA binding protein. Additionally, or alternatively, the peptide sequence can be reverse translated to generate a cDNA probe. The probes or antibodies can then be used to screen a cDNA library (expression library when antibodies are used) and resulting cDNA clones used to screen a genomic library. The gene encoding the RNA binding protein can then be identified by sequence analysis. The identity of the gene can be confirmed by determining the intron-exon structure of the gene, cloning the exons into a vector and performing in vitro transcription/translation to express the protein or by expressing the protein in vivo. The expressed protein can then be added to the binding solution, the interactions with the RNA molecules detected and compared with the interactions of the original RNA binding protein and RNA molecules. The gene is confirmed as encoding the RNA binding protein if the interactions between the test protein and the RNA molecules and the original protein and RNA molecules are substantially the same. Procedures for all of these manipulations are well established and known to those of skill in the art and/or are described herein.

G. Identifying Regions In RNA Molecules That Interact With RNA Binding Proteins

Regions in RNA molecules that interact with RNA binding proteins can be identified by forming a binding solution comprising (1) an RNA molecule from a subset of RNA molecules consisting of successively smaller fragments of a larger RNA molecule previously identified to be involved in an RNA-protein interaction, or (2) an RNA molecule containing one or more mutations or deletions in a previously identified RNA molecule involved in an RNA-protein interaction, buffer components comprising a buffer, a monovalent cation, a divalent cation, a reducing agent, and a density agent, and non-specific competitors, adding one or more RNA binding proteins, and detecting the interaction between the RNA molecule and the RNA binding proteins. By comparing which RNA molecules interact with the binding proteins to those which do not interact, the region of the RNA molecule involved in the interaction can be identified. An assay of this type can identify all the regions in an RNA molecule involved in an interaction with an RNA binding protein as well as identifying the specific nucleotides that interact with the RNA binding protein.

H. Identifying Regions in RNA Binding Proteins That Interact With RNA Molecules

Regions in RNA binding proteins that interact with RNA molecules can be identified by forming a binding solution comprising one or more RNA molecules, buffer components comprising a buffer, a monovalent cation, a divalent cation, a reducing agent, and a density agent, and non-specific competitors, and adding one or more fragments of an RNA binding protein that were obtained by peptidase digestion of an RNA binding protein or by peptide synthesis, and detecting the interactions of the RNA binding protein peptides with the RNA molecules. This is feasible since the portion of an RNA binding protein that interacts with an RNA molecule is generally a self-contained domain. By comparing which peptides are involved in an interaction with an RNA molecule and which are not, the region of the RNA binding protein involved in the interaction can be identified. Identification of the specific amino acids involved in the interaction of the RNA binding protein with the RNA molecules can be accomplished by making mutations in the peptide fragments that interact with the RNA molecules and testing the mutated peptides for interactions with RNA molecules. The amino acids that are involved in the interaction of the RNA binding protein with the RNA molecule will be identified by the mutated peptides that do no interact with the RNA molecule.

I. Screening For Compounds That Modulate Interaction Of RNA Molecules And RNA Binding Proteins Identification of compounds that modulate the interaction of RNA molecules and RNA binding proteins can be accomplished by including one or more test compounds in the binding solution comprising the RNA molecules of interest, the RNA binding proteins of interest, and buffer components comprising a buffer, a monovalent cation, a divalent cation, a reducing agent, and a density agent, and non-specific competitors, and detecting the interaction between the RNA molecules and the RNA binding proteins. Test compounds that modulate the interaction between the RNA molecules and RNA binding proteins can be identified by comparing the interactions in the binding solution that does not contain the test compound with the interactions in the binding solution containing the test compounds. Binding solutions that include one or more test compounds are referred to herein as test solutions. Compounds that modulate the interaction will be identified if the interactions in the two solutions differ. An assay of this type can be used to identify compounds that modulate the interaction by binding to the RNA molecules or by binding to the RNA binding proteins in a given sample. The identification of such compounds can lead to the development of therapies to treat a variety of diseases.

EXAMPLES

Example 1

Development of Optimum Universal Assay Conditions.

Universal conditions for the assay to detect interaction between RNA binding proteins and RNA molecules were optimized using gel mobility shift to detect interactions. The assay was performed generally as described above. Specifically, a binding solution was formed by mixing an RNA binding protein sample, an RNA molecule, and buffer components. The buffer components included a buffer, a monovalent cation, a divalent cation, a reducing agent, and a density agent. The type and concentration of the various buffer components were varied to assess their effect on binding and to determine which composition of the buffer components facilitated interactions of RNA binding proteins with a variety of RNA molecules.

RNA Binding Proteins: A protein extract from SH-SY5Y cells was used as the RNA binding protein sample. Protein extracts have also been prepared and tested from numerous other cell lines including HeLa, K562 and primary astrocytes and from tissue samples, for example, rat brain. The SH-SY5Y extract was prepared as follows. A sample of SH-SY5Y cells was divided into 10 large cultures 30 ml each in T150 flasks ($9.9 \times 10^5$ cells/flask). The media was removed, the cells were placed in 150 cc dishes, washed in 1× PBS, and scraped in PBS. The cells were then counted as follows: $(73 \times 10^4$ cells/ml)×(42 ml)×(10 (×dil))=$3.1 \times 10^8$ cells total. After counting, the PBS was removed and 400 μl lysis buffer (per dish) was added. The lysis buffer had the following composition:

| 10 ml | stock concentration | final concentration |
| --- | --- | --- |
| 250 μl | 1 M Tris HCl (pH 7.9) | 25 mM Tris-HCl (pH 7.9) |
| 20 μl | 50 mM EDTA | 0.5 mM EDTA |
| 100 μl | 10 mM PMSF | 0.1 mM phenylmethyl sulfonyl fluoride |
| 100 μl | 200 mM sodium fluoride | 2 mM sodium fluoride |
| 100 μl | 200 mM sodium pyro-phosphate | 2 mM sodium pyro-phosphate |

The cells were then frozen at −20° C. for 30 minutes, thawed, and centrifuged at 15000 g at 4° C. for 15 minutes. The supernatant was divided into 100 μl aliquots and stored at −80° C.

RNA Molecules: AUUUA, amyloid precursor protein (APP) untranslated region (UTR), and poly(A) were used as the RNA molecules in separate assays. These were chosen to assess the ability of the assay to detect interactions using disparate RNA molecules. The RNA molecules were prepared by in vitro transcription by SP6 or T7 RNA polymerase. To facilitate detection of interactions, $^{32}$P-UTP was incorporated into the RNA molecules during transcription. Many in vitro transcription kits are commercially available and optimized for efficient RNA synthesis. The RNA molecules were prepared generally as described by Sambrook et al. and Ausubel et al. Briefly, a reaction mix containing 2 μl 10× transcription buffer (400 mM Tris-HCl, pH 7.5, 60 mM MgCl$_2$, 20 mM spermidine, 50 mM NaCl), 1 μl each of ATP, CTP, and GTP (10 mM), 2 μl 50 μM UTP, 2.5 μl $^{32}$P-UTP, 2 μl linear transcription template (approximately 100 ng) and 2 μl enzyme mix (RNase Inhibitor and 20 U RNA polymerase) was prepared in a final volume of 20 μl. Unless otherwise indicated, all dilutions were made with DEPC treated water. This reaction mixture was incubated for 2 hours at 37° C. Then 1 μl of RNase-free DNase I was added and the reaction incubated for 15 minutes at 37° C. Finally, 20 μl water and 40 μl phenolchloroform were added and the reaction was extracted. The unincorporated nucleotides are then removed by gel filtration through G-25 spin columns.

Optimizing Buffer: The first variable in the assay is the buffer. Tris, HEPES, and Bis-Tris Propane (BTP), were tested for efficiency at promoting interactions with the test RNA molecules. For these assays the buffer was at a concentration of 7.5 mM and the binding solution included 10 mM KCl, 0.2 mM DTT, 10% glycerol, and 0.2 μg/μl tRNA as competitor for non-specific RNA/protein interactions. Assays were also performed to determine the optimum pH for the buffer. The buffers studied were HEPES at pH 8, Bis-Tris Propane at pH 8 and 7.5, and Tris at pH 8 and pH 7.4. All three buffers allowed for the binding interaction for all three RNA molecules. While there was little difference between them, the use of BTP resulted in significant binding in all cases and, since it has the largest range of buffering capacity, was chosen as the buffer for further optimization.

For all RNA molecules studied, the optimal pH appeared to be 8 or 9. Significant binding was observed for each RNA molecule at pH 10, a condition in which RNase $T_1$ inhibition becomes evident. Conversely low pH seems to inhibit binding. The results are summarized in the table below:

| | pH | | | | |
|---|---|---|---|---|---|
| RNA | 6 | 7 | 8 | 9 | 10 |
| APP | − | − | + | ++ | ++ |
| AUUUA | − | ++ | ++ | ++ | ++ |
| poly(A) | − | ++ | ++ | ++ | + |

Based on these results, the preferred assay will be composed of RNase $T_1$, tRNA as the non-specific competitor, and a buffer consisting of BTP at pH 8.5.

Optimizing Cations: The final aspect of kit development was the optimization of monovalent and divalent cations. Three monovalent ($K^+$, $Na^+$, and $NH_4^+$) and three different divalent cations ($Mg^{++}$, $Ca^{++}$, and $Fe^{++}$) were analyzed. These were tested at various concentrations (0, 0.1, 1, 10, 50, 100 and 250 mM). The optimal monovalent cation was then tested with the individual divalent cation concentrations and vice versa.

Three monovalent ($K^+$, $Na^+$, and $NH_4^+$) cations were first tested at concentrations ranging from 0 to 500 mM. Initially, 0, 0.2, 2, 12.5, 20, and 50 mM concentrations of each cation were tested for effects on RBP/RNA complex formation for APP, AUUUA, and poly(A). The SH-SY5Y protein extract and a binding buffer consisting of 20 mM Bis-Tris propane at pH 9.0, previously demonstrated to result in optimal binding interactions, were used in addition to the cation and probe. No significant differences were noted for either concentration or cations at 0 to 50 mM. Higher concentrations were then tested.

The studies of divalent cation effects of RBP/RNA interactions were also initiated. The concentration effect of $Mg^{++}$ on the complex formation between APP RNA and proteins (SH-SY5Y) was examined first. The results showed that at lower concentrations ($\leq 10$ mM) of $Mg^{++}$, normal complex formation was observed. At higher concentrations (10 mM, 50 mM, 100 mM, 250 mM) $Mg^{++}$ inhibited the interaction between APP RNA and proteins to differing degrees.

The wide concentration range of monovalent cations capable of promoting interactions compared to the relatively narrow range for divalent is likely due to APP adapting tertiary structures which depend on divalent cations. This would suggest that AUUUA and poly(A) interactions may not be as dependent on divalent cations since they are presumably linear structures.

The concentration effects of divalent cations ($Mg^{++}$, $Ca^{++}$ and $Fe^{++}$) on the complex formation between APP, AUUUA and poly(A) RNA and proteins (SH-SY5Y) were then examined. The results demonstrated that 1 mM for all three divalent cations is the optimal concentration for the detection of interactions between RNAs (APP, AUUUA and poly(A)) and proteins (SH-SY5Y) under the selected binding condition. At higher concentration (10 mM, 50 mM, 100 mM, 250 mM), $Mg^{++}$, $Ca^{++}$ and $Fe^{++}$ inhibited the complex formation to varying degrees. Following a comparison of all three divalent cations at the optimal concentration for binding interactions (1 mM), $Mg^{++}$ was selected for further studies.

The effects of individual monovalent salt concentrations (0, 50, 100, and 500 mM) on AUUUA, APP, and poly(A) RNA's binding to SH-SY5Y protein were also completed. The monovalent cations used were $K^+$, $Na^+$ and $NH_4^+$. RNA-protein complexes form in a much broader monovalent salt concentration (0 to 100 mM) than was observed for the divalent cations (0 to 5 mM) with the optimal monovalent salt concentration being determined to be 50 mM. The binding interaction with the cis-element of APP for all three monovalent cations was compared at 50 mM and KCl was chosen based on its ability to promote the RBP/RNA interaction.

The monovalent ($K^+$) and divalent ($Mg^{++}$) cations were then combined to determine the best concentrations use in the development of the detection kit. Combinations of 10, 50 and 100 mM $K^+$ with 1 mM $Mg^{++}$ and 0.1 mM, 1 mM, and 2.5 mM $Mg^{++}$ with 50 mM $K^+$ were analyzed. The results showed that the combination of 50 mM $K^+$ with 1 mM $Mg^{++}$ is better than the other combinations for detecting APP RNA-protein interactions. This result was confirmed by using AUUUA RNA and poly(A) RNA.

Use of Reducing Agents: The effects of reducing agents were studied by comparing the binding reaction under the previously established conditions (0.2 mM DTT), substituting 0.2 mM β-mercaptoethanol for the DTT, or in the absence of a reducing agent. In five of the six interactions studied, the presence or absence of reducing agent had no effect on the binding interaction. Similarly, no effect of reducing agent was observed with poly(A) RNA and binding protein derived from K562 cells. However, when binding protein was isolated from HeLa cells, a reproducible effect was observed with DTT enhancing the interaction better than β-mercaptoethanol which in turn was better than no reducing agent. The requirement of DTT for certain reactions suggests that its use is preferred as a component of the buffer.

Use of Density Agents: The binding efficiencies of six different RNAs were tested in the presence of 10% glycerol, 10% polyethylene glycol, or no density agent, under buffer, cation and reducing conditions described above. Although no quantitative differences were detected, the addition of glycerol or PEG enhanced the quality of the band on the gel mobility assay. In the absence of a density agent the bands were clearly more diffuse. Thus, while not required, the addition of 10% glycerol is preferred.

Based on this work, the optimal buffer components were determined to be BTP at pH 8.5, 50 mM KCl, 1 mM $MgCl_2$, 0.2 mM DTT and 10% glycerol. These conditions have been used for further validating assays as described below. A BTP concentration of 7.5 mM was used.

Heating Step: The next phase involved screening twelve other RNA elements for detection of interactions under the selected conditions. These assays were also run in the presence of specific and non-specific competitor RNA. The first two cis-elements studied were the Iron Response Element (IRE) and histone RNA. In each case, binding was detected but very inefficiently. Since these had been reported to form secondary structures, we heated the labeled RNA to 80° C. and then cooled the sample to 37° C. after forming the binding solution and before adding the RNA binding proteins. This was intended to break any incorrect structures that may have formed in the RNA and it greatly facilitated the detection of interactions. For both cis-elements specific interactions were detected under our conditions. RNAs of various sizes and structures have been tested under the above conditions and shown to form interactions with binding proteins consistent with those reported in the literature.

The binding proteins tested contain various motifs, including RGG boxes, KH domains and Arg-rich proteins.

The preferred method for detecting interactions between RNA molecules and RNA binding proteins involves (1) forming a binding solution including RNA molecules, BTP at pH 8.5, 50 mM KCl, 1 mM $MgCl_2$, 0.2 mM DTT, and 10% glycerol, (2) heating the binding solution to denature the RNA molecules, (3) cooling the binding solution, (4) adding RNA binding proteins to the binding solution, and (5) detecting the interactions between the RNA molecules and the RNA binding proteins.

Example 2
Assays Using Universal Conditions.

Figure 1:
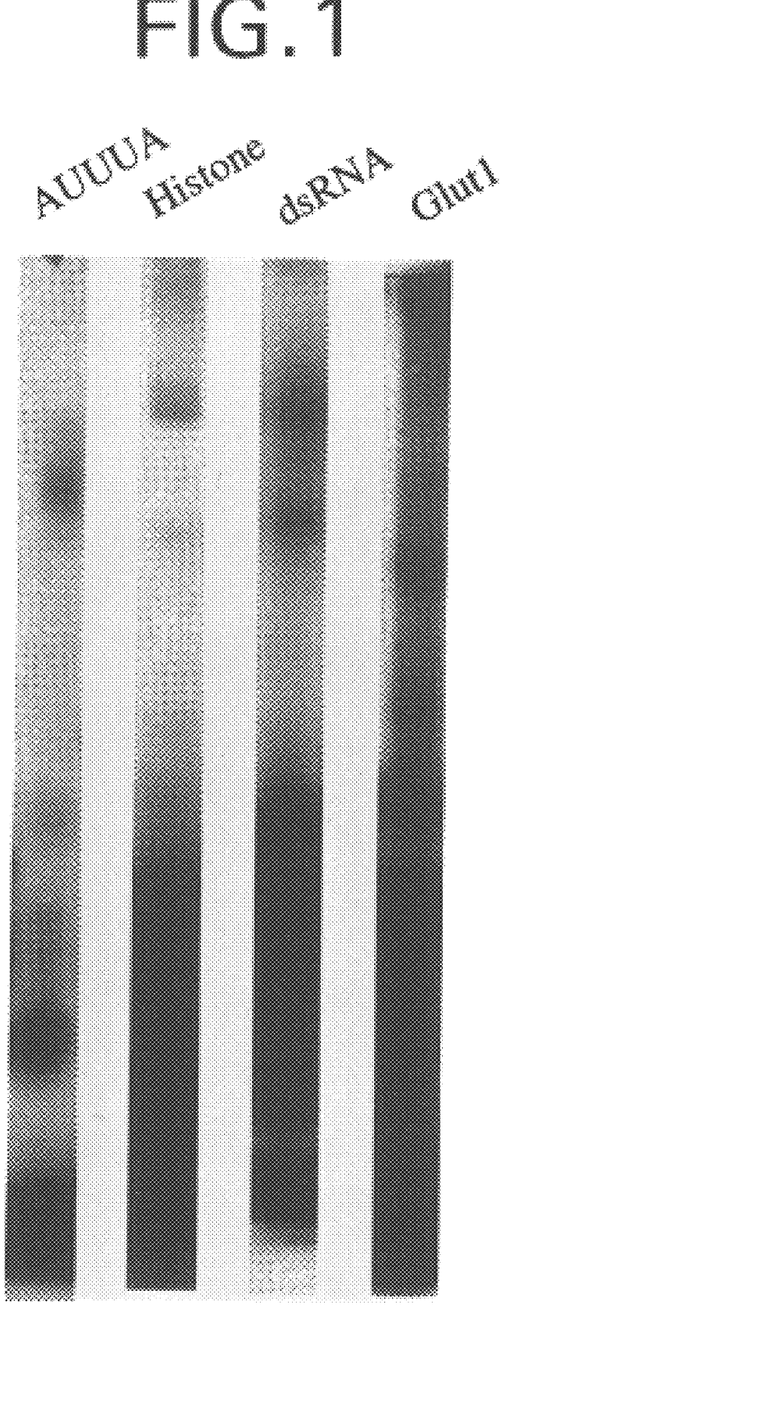
FIG. 1 is a digitized image of a gel mobility shift assay gel showing the relative migration of radioactive RNA molecules. Four different radioactive RNA molecules, AUUUA, histone, double-stranded RNA (dsRNA), and the glucose transporter type 1 (Glut1) 5' untranslated region, were incubated with either SH-SY5Y or CHL/260 protein extract and altered mobility of the RNA molecules in a gel is indicated by slow migrating radioactive bands or smears.

Several assays were performed demonstrating the usefulness of the universal assay conditions described in Example 1 for detecting interactions between various RNA molecules and RNA binding proteins. In the first assay, interactions of several RNA molecules (radioactively labelled) with different recognition features were incubated with SH-SY5Y or CHL/260 protein extract. The RNA molecules were chosen to highlight detection of interactions dependent on RNA sequence (AUUUA RNA), sequence and RNA structure (histone RNA), or RNA structure alone (double-stranded RNA). In addition to these small RNA molecules (less than 30 nucleotides), the 210 nucleotide 5' untranslated region of glucose transporter type 1 (Glut1) was also tested. The results are shown in FIG. 1. SH-SY5Y protein extract was used with AUUUA RNA and CHL/260 protein extract was used with the remaining RNA molecules. The multiple slower migrating bands in each of the lanes indicate that the universal assay conditions allow detection of interactions between RNA molecules and RNA binding proteins across the spectrum of interaction types.

Figure 2:
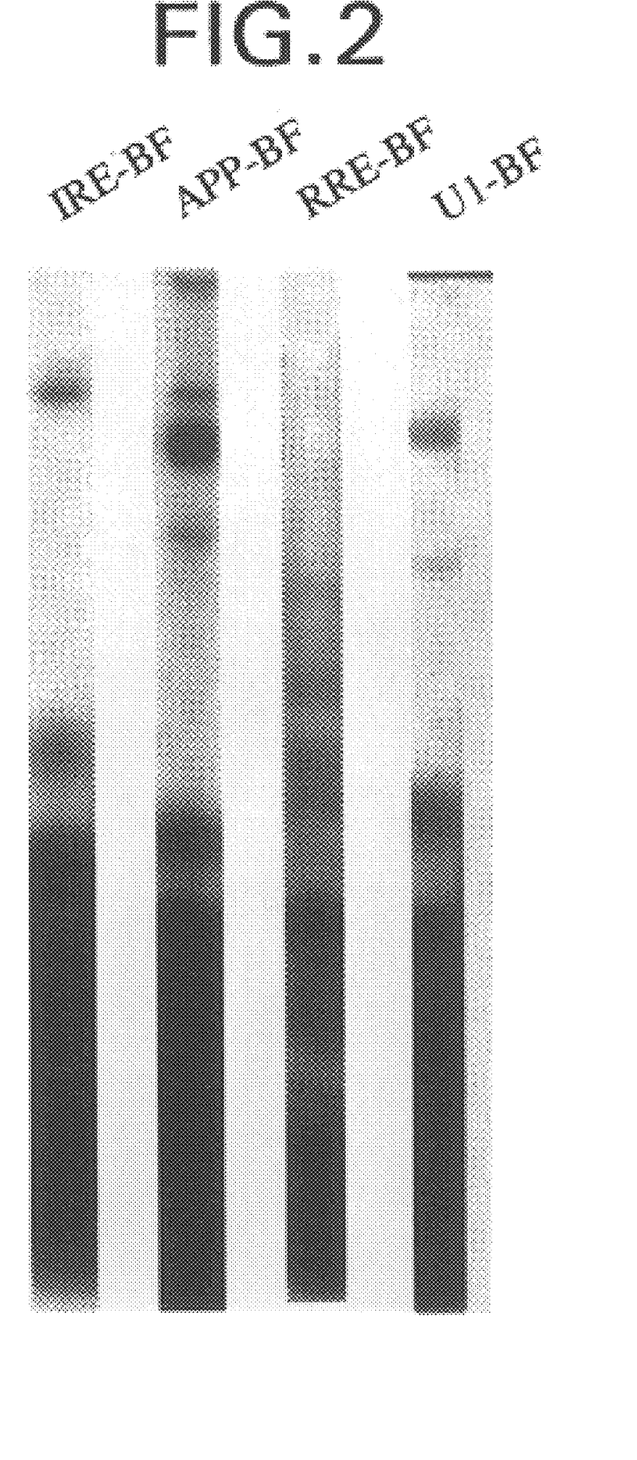
FIG. 2 is a digitized image of a gel mobility shift assay gel showing the relative migration of radioactive RNA molecules. Four different radioactive RNA molecules representing the targets of specific RNA binding protein motif were incubated with SH-SY5Y or CHL/260 protein extract or recombinant Rev protein and altered mobility of the RNA molecules in a gel is indicated by slow migrating radioactive bands or smears. The RNA molecules represent targets for RNA binding proteins containing double-stranded RNA binding motifs (IRE-BF), RGG box (APP-BF), Arg-rich motifs (RRE-BF), and RNP motifs (U1-BF).

In another assay, interactions of several RNA molecules representing targets for different binding motifs were incubated with SH-SY5Y or CHL/260 protein extract or recombinant Rev protein. The RNA molecules were chosen to highlight detection of interactions involving RNA binding proteins containing double-stranded RNA binding motifs (IRE-BF), RGG box (APP-BF), Arg-rich motifs (RRE-BF), and RNP motifs (U1-BF). The results are shown in FIG. 2. SH-SY5Y protein extract was used in the APP-BF assay, CHL/260 protein extract was used with the IRE-BF and U1-BF assays, and recombinant Rev protein was used with the RRE-BF assay. The multiple slower migrating bands in each of the lanes indicate that the universal assay conditions allow detection of interactions between RNA molecules and RNA binding proteins across the spectrum of interaction types.

Figure 3:
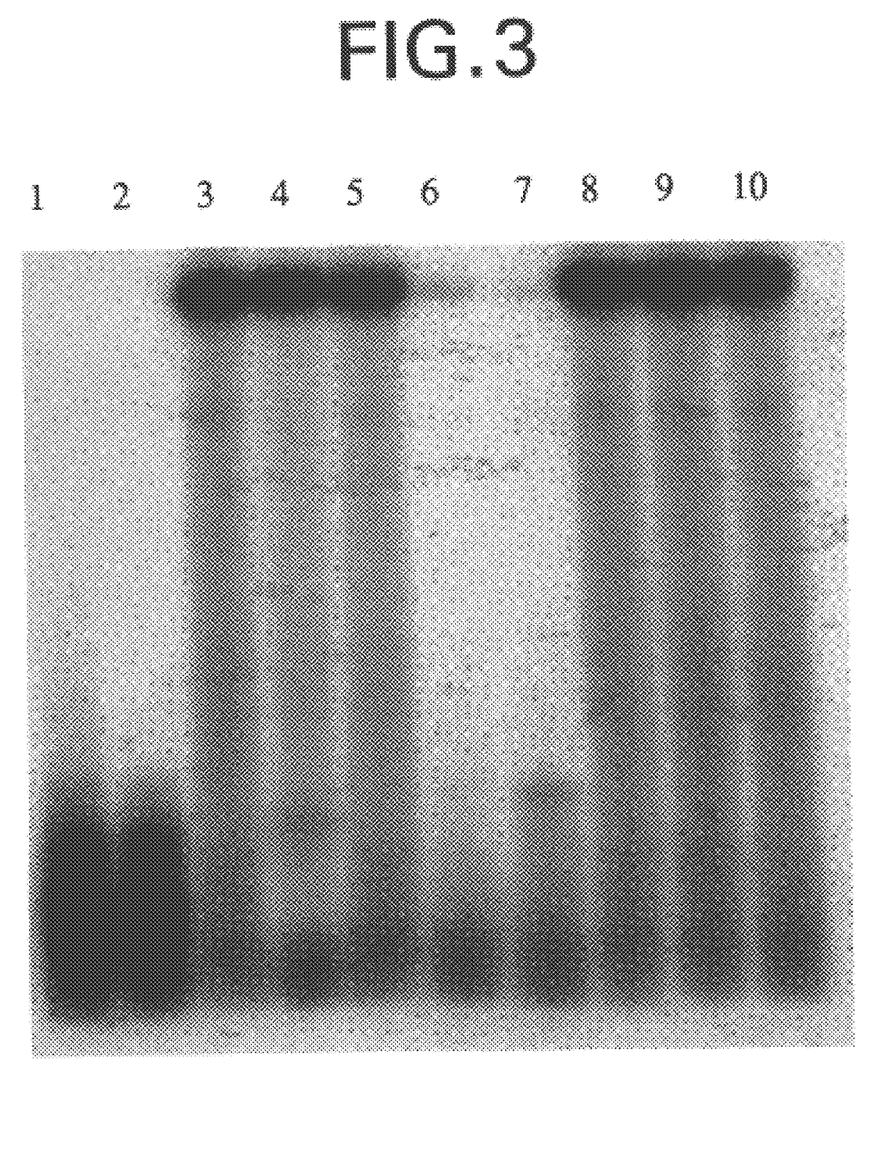
FIG. 3 is a digitized image of a gel mobility shift assay gel showing the relative migration of radioactive RNA molecules. Radioactive RNA molecule IRE was incubated in the presence (lanes 3–10) or absence (lanes 1 and 2) of K562 protein extract and altered mobility of the RNA molecules in a gel is indicated by slow migrating radioactive bands or smears. Assays run in lanes 5–7 were incubated in the presence of increasing concentrations (100×, 1,000×, and 10,000×, respectively) of unlabelled IRE. Assays run in lanes 8–10 were incubated in the presence of similar concentrations of a mutant IRE which is defective for binding.

In another assay, the specificity of the interaction being detected was confirmed. Radioactively labelled IRE RNA was incubated in the presence or absence of K562 protein extract. To test whether interactions detected were specific or not, unlabelled IRE was also included in some of the assays. This RNA competes with the labelled IRE RNA for interaction with RNA binding proteins. As a control, unlabelled mutant IRE (which is defective for binding) was included in some assays. If the interaction is specific, this RNA should not compete with the labelled IRE RNA for the RNA binding proteins. The results of these assays are shown in FIG. 3. Lanes 1 and 2, where no protein extract was included, show no mobility shift, as expected. Lanes 3 and 4, where protein extract was included, show a clear mobility shift. Lanes 5–7 show assays where increasing concentrations (100×, 1,000×, and 10,000×, respectively) of unlabelled IRE RNA was included. This unlabelled RNA effectively competes with the labelled RNA for interaction with the RNA binding proteins as can be seen for the abolition of mobility shift in lanes 6 and 7. Lanes 8–10 show assays where increasing concentrations (100×, 1,000×, and 10,000×, respectively) of mutant IRE RNA was included. This unlabelled RNA is unable to compete with the labelled RNA for interaction with the RNA binding proteins as can be seen from the unchanged mobility shift in lanes 8–10. This clearly shows that the competitive effect of unlabelled IRE RNA seen in lanes 6 and 7 is not due to non-specific interactions between the RNA molecules and the RNA binding proteins.

The universal assay conditions are also beginning to be used in high throughput screening assays for compound isolation. Such assays will analyze combinatorial libraries for compounds capable of altering the binding properties of the RBP to the RNA, with the RNA being targeted. The information obtained from RNA mapping and peptide mapping will be used in molecular modeling to rationally design compounds capable of modulating the interaction of the RNA binding protein with the RNA molecule.

Those skilled in the art will recognize, or be able to ascertain using no more than routine experimentation, many equivalents to the specific embodiments of the invention described herein. Such equivalents are intended to be encompassed by the following claims. The references cited herein are hereby incorporated by reference.

I claim:

1. A method for detecting interactions between RNA binding proteins and RNA molecules, wherein the method is performed under conditions that permit detection of interactions between RNA binding proteins and each of amyloid precursor protein untranslated region, AUUUA, and poly(A), the method comprising forming a binding solution comprising one or more different RNA molecules, and buffer components comprising a buffer, a monovalent cation, a divalent cation, a reducing agent, and a density agent for enhancing gel band quality, heating the binding solution for a time and to a temperature sufficient to denature the one or more RNA molecules, cooling the binding solution, adding one or more different RNA binding proteins to the binding solution, and detecting interactions between the one or more RNA binding proteins and the one or more RNA molecules.

2. The method of claim 1 wherein the buffer is (1) selected from the group consisting of HEPES, Tris, and Bis-Tris Propane, and (2) at a pH between about 8 and 10, wherein the monovalent cation is selected from the group consisting of $K^+$, $Na^+$, and $NH_4^+$, wherein the divalent cation is selected from the group consisting of $Mg^{++}$, $Ca^{++}$, and $Fe^{++}$, wherein the reducing agent is selected from the group consisting of dithiothreitol and β-mercaptoethanol, and wherein the density agent is selected from the group consisting of glycerol and polyethylene glycol.

3. The method of claim 2 wherein the buffer is (1) selected from the group consisting of HEPES, Tris, and Bis-Tris Propane, (2) at a pH between about 8 and about 10, and (3) at a concentration of between about 5 and about 100 mM, wherein the monovalent cation is $K^+$ at a concentration of about 50 mM, wherein the divalent cation is $Mg^{++}$ at a concentration of about 1 mM, wherein the reducing agent is dithiothreitol at a concentration of about 0.2 mM, and wherein the density agent is glycerol at a concentration of about 10 percent (v/v), (b) buffer components wherein the buffer is Bis-Tris Propane at a pH of about 8.5 and at a concentration of about 7.5 mM, wherein the monovalent cation is (1) selected from the group consisting of $K^+$, $Na^+$, and $NH_4^+$, and (2) at a concentration of between 0 and about 100 mM, wherein the divalent cation is $Mg^{++}$ at a concentration of about 1 mM, wherein the reducing agent is dithiothreitol at a concentration of about 0.2 mM, and wherein the density agent is glycerol at a concentration of about 10 percent (v/v), (c) buffer components wherein the buffer is Bis-Tris Propane at a pH of about 8.5 and at a concentration of about 7.5 mM, wherein the monovalent cation is $K^+$ at a concentration of about 50 mM, wherein the divalent cation is (1) selected from the group consisting of $Mg^{++}$, $Ca^{++}$, and $Fe^{++}$, and (2) at a concentration of between 0 and about 5 mM, wherein the reducing agent is dithiothreitol at a concentration of about 0.2 mM, and wherein the density agent is glycerol at a concentration of about 10 percent (v/v), (d) buffer components wherein the buffer is Bis-Tris Propane at a pH of about 8.5 and at a concentration of about 7.5 mM, wherein the monovalent cation is $K^+$ at a concentration of about 50 mM, wherein the divalent cation is $Mg^{++}$ at a concentration of about 1 mM, wherein the reducing agent is (1) selected from the group consisting of dithiothreitol and β-mercaptoethanol, and (2) at a concentration of between 0 and about 1 mM, and wherein the density agent is glycerol at a concentration of about 10 percent (v/v), and (e) buffer components wherein the buffer is Bis-Tris Propane at a pH of about 8.5 and at a concentration of about 7.5 mM, wherein the monovalent cation is $K^+$ at a concentration of about 50 mM, wherein the divalent cation is $Mg^{++}$ at a concentration of about 1 mM, wherein the reducing agent is dithiothreitol at a concentration of about 0.2 mM, and wherein the density agent is (1) selected from the group consisting of glycerol and polyethylene glycol, and (2) at a concentration of between about 1 and about 20 percent (v/v).

4. The method of claim 3 wherein the buffer is Bis-Tris Propane at a pH of about 8.5 and at a concentration of about 7.5 mM, wherein the monovalent cation is $K^+$ at a concentration of about 50 mM, wherein the divalent cation is $Mg^{++}$ at a concentration of about 1 mM, wherein the reducing agent is dithiothreitol at a concentration of about 0.2 mM, and wherein the density agent is glycerol at a concentration of about 10 percent (v/v).

5. The method of claim 1 wherein at least one of the RNA binding proteins or at least one of the RNA molecules is labeled with a detectable group, and wherein detecting interactions between the one or more RNA binding proteins and the one or more RNA molecules is accomplished by separating complexes of interacting RNA binding proteins and RNA molecules from RNA binding proteins and RNA molecules not involved in an interaction, and measuring the labeled RNA binding proteins or labeled RNA molecules involved in interactions.

6. The method of claim 5 wherein separating complexes of interacting RNA binding proteins and RNA molecules from RNA binding proteins and RNA molecules not involved in an interaction is accomplished by gel electrophoresis or filter binding.

7. The method of claim 1 wherein detecting interactions between the one or more RNA binding proteins and the one or more RNA molecules is facilitated by separating complexes of interacting RNA binding proteins and RNA molecules from RNA binding proteins and RNA molecules not involved in interactions, and analyzing the RNA molecules or RNA binding proteins involved in interactions.

8. The method of claim 1 further comprising comparing the interactions of the one or more RNA binding proteins and the one or more RNA molecules in the presence and absence of one or more competing RNA molecules.

9. The method of claim 1 wherein the binding solution comprises one or more RNA molecules and buffer components, and wherein one RNA binding protein is added to the binding solution.

10. The method of claim 9 further comprising identifying RNA molecules that interact with the RNA binding protein.

11. The method of claim 10 wherein identifying RNA molecules that interact with the RNA binding protein is accomplished by nucleic acid sequencing.

12. A method of comparing the interactions of the RNA binding protein and RNA molecules in the presence and absence of competing RNA molecules, the method comprising identifying RNA molecules according to the method of claim 10 and comparing the interactions of the RNA binding protein and the one or more RNA molecules in the presence and absence of one or more competing RNA molecules.

13. A method of identifying genes encoding RNA molecules that interact with the RNA binding protein, the method comprising identifying RNA molecules according to the method of claim 10 and identifying one or more genes encoding one or more of the RNA molecules that interact with the RNA binding protein.

14. The method of claim 10 wherein the RNA molecules are portions of an RNA molecule encoded by a gene.

15. A method of identifying regions of RNA binding proteins that interact with RNA molecules, the method comprising detecting interactions according to the method of claim 10 and identifying regions of the RNA binding protein that interact with the one or more RNA molecules.

16. The method of claim 15 wherein identifying regions of the RNA binding protein that interact with the RNA binding proteins is accomplished by detecting interactions between the one or more RNA molecules and portions of the RNA binding protein.

17. A method of identifying compounds that modulate interaction of RNA molecules and the RNA binding protein, the method comprising detecting interactions according to the method of claim 10 and forming a test solution comprising the one or more RNA molecules, the buffer components, and a test compound, wherein the buffer components are the same as those in the binding solution, heating the test solution for a time and to a temperature sufficient to denature the one or more RNA molecules, cooling the test solution, adding the RNA binding protein to the test solution, detecting interactions between the one or more RNA molecules and the RNA binding protein in the test solution, and comparing the interactions detected in the binding solution with the interactions detected in the test solution, wherein the test compound is identified as a compound that modulates interaction of the RNA molecules and the RNA binding protein if the interactions detected in the binding solution and the interactions detected in the test solution differ.

18. The method of claim 1 wherein the binding solution consists of one RNA molecule and the buffer components.

19. The method of claim 18 wherein the RNA molecule is encoded by a gene of interest.

20. A method of identifying RNA binding proteins that interact with the RNA molecule, the method comprising detecting interactions according to the method of claim 19 and identifying the RNA binding proteins that interact with the RNA molecule, wherein identifying RNA binding proteins that interact with the RNA molecule is accomplished by analyzing the RNA binding proteins involved in the interactions.

21. The method of claim 20 wherein analyzing the RNA binding proteins involved in the interactions is accomplished by antibody detection, peptide mapping, or amino acid sequencing.

22. The method of claim 18 further comprising comparing the interactions of the one or more RNA binding proteins and the RNA molecule in the presence and absence of one or more competing RNA molecules.

23. The method of claim 18 further comprising identifying regions in the RNA molecule that interact with the one or more RNA binding proteins.

24. The method of claim 23 wherein identifying regions of the RNA molecule that interact with the RNA binding proteins is accomplished by analyzing the RNA molecule involved in the interactions.

25. The method of claim 24 wherein analyzing the RNA molecule involved in the interactions is accomplished by digesting unprotected regions of the RNA molecule involved in the interactions and nucleic acid sequencing.

26. A method of identifying compounds that modulate interaction of RNA binding proteins and the RNA molecule, the method comprising detecting interactions according to the method of claim 18 and forming a test solution comprising the RNA molecule, the buffer components, and a test compound, wherein the buffer components are the same as those in the binding solution, heating the test solution for a time and to a temperature sufficient to denature the one or more RNA molecules, cooling the test solution, adding the one or more RNA binding proteins to the test solution, detecting interactions between the one or more RNA binding proteins and the RNA molecule in the test solution, and comparing the interactions detected in the binding solution with the interactions detected in the test solution, wherein the test compound is identified as a compound that modulates interaction of the RNA binding proteins and the RNA molecule if the interactions detected in the binding solution and the interactions detected in the test solution differ.

27. A method for detecting interactions between RNA binding proteins and RNA molecules, the method comprising (a) selecting conditions that permit detection of interactions between RNA binding proteins and each of amyloid precursor protein untranslated region, AUUUA, and poly(A), (b) forming a binding solution comprising one or more different RNA molecules, and buffer components comprising a buffer, a monovalent cation, a divalent cation, a reducing agent, and a density agent for enhancing gel band quality, (c) heating the binding solution for a time and to a temperature sufficient to denature the one or more RNA molecules, (d) cooling the binding solution, (e) adding one or more different RNA binding proteins to the binding solution, and (f) detecting interactions between the one or more RNA binding proteins and the one or more RNA molecules.

28. The method of claim 2 wherein the buffer is Bis-Tris Propane at a pH of about 8.5 and at a concentration of about 7.5 mM, wherein the monovalent cation is (1) selected from the group consisting of $K^+$, $Na^+$, and $NH_4^+$, and (2) at a concentration of between 0 and about 100 mM, wherein the divalent cation is $Mg^{++}$ at a concentration of about 1 mM, wherein the reducing agent is dithiothreitol at a concentration of about 0.2 mM, and wherein the density agent is glycerol at a concentration of about 10 percent (v/v).

29. The method of claim 2 wherein the buffer is Bis-Tris Propane at a pH of about 8.5 and at a concentration of about 7.5 mM, wherein the monovalent cation is $K^+$ at a concentration of about 50 mM, wherein the divalent cation is (1) selected from the group consisting of $Mg^{++}$, $Ca^{++}$, and $Fe^{++}$, and (2) at a concentration of between 0 and about 5 mM, wherein the reducing agent is dithiothreitol at a concentration of about 0.2 mM, and wherein the density agent is glycerol at a concentration of about 10 percent (v/v).

30. The method of claim 2 wherein the buffer is Bis-Tris Propane at a pH of about 8.5 and at a concentration of about 7.5 mM, wherein the monovalent cation is $K^+$ at a concentration of about 50 mM, wherein the divalent cation is $Mg^{++}$ at a concentration of about 1 mM, wherein the reducing agent is (1) selected from the group consisting of dithiothreitol and β-mercaptoethanol, and (2) at a concentration of between 0 and about 1 mM, and wherein the density agent is glycerol at a concentration of about 10 percent (v/v).

31. The method of claim 2 wherein the buffer is Bis-Tris Propane at a pH of about 8.5 and at a concentration of about 7.5 mM, wherein the monovalent cation is $K^+$ at a concentration of about 50 mM, wherein the divalent cation is $Mg^{++}$ at a concentration of about 1 mM, wherein the reducing agent is dithiothreitol at a concentration of about 0.2 mM, and wherein the density agent is (1) selected from the group consisting of glycerol and polyethylene glycol, and (2) at a concentration of between about 1 and about 20 percent (v/v).

32. The method of claim 1 wherein the binding solution comprises three or more RNA molecules and buffer components.

33. The method of claim 1 wherein three or more RNA binding proteins are added to the binding solution.

34. A method for detecting interactions between RNA binding proteins and RNA molecules, the method comprising (a) forming a binding solution comprising one or more different RNA molecules, and buffer components comprising a buffer, a monovalent cation, a divalent cation, a reducing agent, and a density agent for enhancing gel band quality, (b) heating the binding solution for a time and to a temperature sufficient to denature the one or more RNA molecules, (c) cooling the binding solution, (d) adding one or more different RNA binding proteins to the binding solution, and (e) detecting interactions between the one or more RNA binding proteins and the one or more RNA molecules, wherein conditions are selected to be conditions that would permit, in a separate performance of steps (a) through (e), detection of interactions between RNA binding proteins and each of amyloid precursor protein untranslated region, AUUUA, and poly(A).

* * * * *